(12) United States Patent
Alterman et al.

(10) Patent No.: US 7,625,838 B2
(45) Date of Patent: Dec. 1, 2009

(54) [1, 2, 4] TRIAZOLO [1, 5-A] PYRIMIDINE DERIVATIVES AS CHROMATOGRAPHIC ADSORBENT FOR THE SELECTIVE ADSORPTION OF IGG

(75) Inventors: Mathias Alterman, Stockholm (SE); Andreas Axen, Uppsala (SE); Enrique Carredano, Uppsala (SE); Anna Gronberg, Uppsala (SE); Jinyu Zou, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 12/486,155

(22) Filed: Jun. 17, 2009

(65) Prior Publication Data

US 2009/0259029 A1  Oct. 15, 2009

Related U.S. Application Data

(63) Continuation of application No. 11/994,145, filed as application No. PCT/SE2006/000808 on Jun. 29, 2006.

(30) Foreign Application Priority Data

Jul. 5, 2005 (SE) .................................. 0501560

(51) Int. Cl.
B01J 20/22 (2006.01)
B01J 20/26 (2006.01)
B01J 20/00 (2006.01)

(52) U.S. Cl. .................... 502/402; 502/401; 502/404
(58) Field of Classification Search ................ 502/401, 502/402, 404
See application file for complete search history.

(56) References Cited

U.S. PATENT DOCUMENTS 4,923,980 A   5/1990   Blomberg 6,117,996 A * 9/2000 Lowe et al. ............... 544/216
6,197,927 B1  3/2001 Braisted et al.

(Continued)

FOREIGN PATENT DOCUMENTS

EP          0 295 073        3/1997

(Continued)

OTHER PUBLICATIONS

Klaus, "Fundamental Solution Properties of 4-Hydroxy-1,3,3a,7-tetrazanlndenes," Journal of Imaging Science and Technology, vol. 42, No. 6, pp. 523-527 (1998).*

(Continued)

Primary Examiner—Jerry Lorengo
Assistant Examiner—Eli Mekhlin
(74) Attorney, Agent, or Firm—Yonggang Ji

(57) ABSTRACT

The present invention relates to a chromatographic adsorbent for selectively adsorbing IgG, comprising the following formula

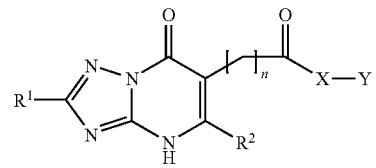

and its corresponding enol-form, wherein X represents O, S, or NH; $R^1$ represents H, $C_{1-6}$ alkyl, $C_{1-6}$ alkoxy, $C_{1-6}$ alkoxy-$C_{1-6}$ alkyl, Ar, —C(O)NHR$^3$, —C(O)—R$^3$ or halo; $R^2$ represents H, $C_{1-3}$ alkyl or halo; $R^3$ represents H, $C_{1-6}$ alkyl, $C_{1-6}$ alkoxy, $C_{1-6}$ alkoxy-$C_{1-6}$ alkyl or Ar; n represents 0, 1, 2 or 3; Y represents a carrier. The present invention also relates to a method of producing said adsorbent as well as use thereof for separating substances by affinity chromatography.

8 Claims, 1 Drawing Sheet

U.S. PATENT DOCUMENTS

| | | |
|---|---|---|
| 6,610,630 B2 | 8/2003 | Schwarz et al. |
| 2003/0166002 A1 | 9/2003 | Chang et al. |
| 2003/0187227 A1 | 10/2003 | Lihme et al. |

FOREIGN PATENT DOCUMENTS

| | | |
|---|---|---|
| EP | 1 500 431 | 1/2005 |
| WO | WO84/00773 | 3/1984 |
| WO | WO97/10887 | 3/1997 |
| WO | WO2004/035199 | 4/2004 |
| WO | WO2004/039765 | 5/2004 |
| WO | WO2004/052870 | 6/2004 |

OTHER PUBLICATIONS

Carredano, E., et al., "A novel and conserved pocket of human k-Fab fragments: Design, synthesis, and verification of directed affinity ligands". Protein Science (2004), 13(6):1476-1488.

Delano, W., et al., "Convergent Solutions to Binding at a Protein-Protein Interface". Science (2000), 287: 1279-1283.

Idusogie, E., et al., "Mapping of the C1q Binding Site on Rituxan, a Chimeric Antibody with a Human IgG1 Fc". Journal of Immunology (2000), 164:4178-4184.

Jones, T. A., et al., "Improved Methods for Building Protein Models in Electron Density Maps and the Location of Errors in these Models". Acta Crystallography (1991), A47:110-119.

Rarey, M., et al., "A Fast Flexible Docking Method using an Incremental Construction Algorithm". Journal of Molecular Biology (1996), 261:470-489.

Teng, S. F., et al., "Affinity chromatography on immobilized 'biomimetic' ligands. Synthesis, immobilization and chromatographic assessment of an immunoglobulin G-binding ligand". Journal of Chromatography B (2000), 740:1-15.

Klaus, R., "Fundamental Solution Properties of 4-Hydroxy-1,3,3a,7-tetraazalndenes", Journal of Imaging Science and Technology (1998), 42(6):523-527.

* cited by examiner

[1, 2, 4] TRIAZOLO [1, 5-A] PYRIMIDINE DERIVATIVES AS CHROMATOGRAPHIC ADSORBENT FOR THE SELECTIVE ADSORPTION OF IGG

CROSS-REFERENCE TO RELATED APPLICATIONS

This application is a continuation of U.S. patent application Ser. No. 11/994,145 filed Dec. 28, 2007, now abandoned, which is a filing under 35 U.S.C. §371 and claims priority to international patent application NO. PCT/SE2006/000808 filed Jun. 29, 2006, published on Jan. 11, 2007, as WO 2007/004954, which claims priority to Swedish patent application number 0501560-7 filed Jul. 5, 2005.

FIELD OF THE INVENTION

The present invention is within the field of chromatographic separation of biomolecules. More closely, it relates to a chromatographic adsorbent comprising a novel ligand selectively adsorbing IgG as well as a method of producing said chromatographic adsorbent and use thereof for affinity chromatography.

BACKGROUND OF THE INVENTION

The development of monoclonal antibody technology has provided an enormous opportunity for science and medicine in implementing research, diagnosis and therapy. Monoclonal antibodies are e.g. used for in vitro and in vivo diagnosis as well as immunotherapy of human disease. At present, a large percentage of the biotechnology-derived drugs under development are based on monoclonal antibodies of type G. IgGs are commonly produced according to standard techniques in large quantities in cellular expression systems. The most widely used production method includes purification via chromatography, which due to its versatility and sensitivity to the compounds often is the preferred purification method in the context of biomolecules.

In the field of affinity chromatography, various patents and patent applications relate to protein A, which is an IgG-binding cell wall protein of the bacteria *Staphylococcus aureus*, and its use as a ligand. For example, PCT/SE83/00297 (Pharmacia Biotech AB) discloses a recombinant form of protein A, wherein a cysteine residue has been added to the protein A molecule to improve its coupling to a separation matrix for subsequent use as an affinity ligand. Further, U.S. Pat. No. 6,197,927 (assigned to Genentech Inc.) discloses Z domain variants of *Staphylococcal* protein A exhibiting an IgG-binding capacity equivalent to the wild type Z domain, but a significantly reduced size. However, Protein A has been shown to be protease sensitive. In addition, protein A-based affinity ligands have also been known to be unstable under acidic and basic conditions, which may result in an undesired leakage of the ligand during the purification process which will both contaminate the product and impair the quality of the purification system.

Within prior art there is a number of patent applications describing small molecule ligands having affinity for IgG:

WO 2004039765 (Amersham Biosciences AB) describes the use of phenyl urea scaffold based small molecules as chromatography affinity ligands for IgG and Fab fragments with light chain of kappa-type.

U.S. Pat. No. 6,610,630 (assigned to Ciphergen Biosystems Inc.) describes the use of 2-mercaptoimidazole and derivatives thereof attached to a solid support as pseudo bio-affinity chromatography media for selective adsorption of IgG.

U.S. Pat. No. 6,117,996 (assigned to Novo Nordisk A/S) describes the preparation of triazine based structures and their use in the purification of various proteinaceous materials.

US 20030166002 (Chang et al) describes the synthesis and selection of active compounds based on triazine structures carrying a linker suited for attachment to a resin.

EP 1500431 (Millipore UK, Ltd, UK) relates to a medium which comprises a solid support and, attached thereto, one or more affinity chromatographic ligands selected from 2-aminobenzimidazole and 2-aminomethylbenzimidazole. The affinity ligands of the invention are used for IgG purification.

In spite of the existing alternatives to Protein A for IgG binding there is still a need of novel IgG-binding ligands of a more advantageous nature. Such new ligands should avoid the above-discussed drawbacks, and preferably also involve more preferable binding properties than the hitherto suggested ligands.

SUMMARY OF THE INVENTION

The present inventors have found a small organic molecule, based on a purine-related structure, that possesses a generic binding of IgG when attached to a chromatographic resin. It may be used as an affinity ligand in IgG purification processes.

In a first aspect, the invention relates to a chromatographic adsorbent for selectively adsorbing IgG, comprising the following formula

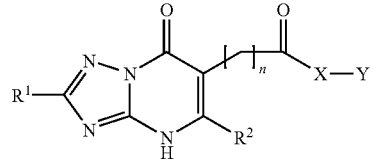

and its corresponding enol-form,
wherein
X represents O, S, or NH;
$R^1$ represents H, $C_{1-6}$ alkyl, $C_{1-6}$ alkoxy, $C_{1-6}$ alkoxy-$C_{1-6}$ alkyl, Ar, —C(O)NHR$^3$, —C(O)—R$^3$ or halo;
$R^2$ represents H, $C_{1-3}$ alkyl or halo;
$R^3$ represents H, $C_{1-6}$ alkyl, $C_{1-6}$ alkoxy, $C_{1-6}$ alkoxy-$C_{1-6}$ alkyl or Ar;
n represents 0, 1, 2 or 3;
Y represents a carrier;
Ar represents a $C_{6-10}$ aryl group, which group is optionally substituted by one or more substituents selected from —OH, cyano, halo, nitro, $C_{1-6}$ alkyl and alkoxy.

The term "halo", when used herein, includes fluoro, chloro, bromo, iodo.

Unless otherwise specified, alkyl groups, and the alkyl parts of alkoxy and alkoxyalkyl, as defined herein may be straight-chain or, when there is a sufficient number (i.e. a minimum of three) of carbon atoms, be branched-chain, and/or cyclic. Further, when there is a sufficient number (i.e. a minimum of four) of carbon atoms, such groups may also be part cyclic/acyclic. Such alkyl groups, and alkyl parts of alkoxy and alkoxyalkyl groups, may be saturated or, when there is a sufficient number (i.e. a minimum of two) of carbon atoms, be unsaturated. Unless otherwise specified, such groups may also be substituted by one or more halo, and especially fluoro, atoms.

For the avoidance of doubt, alkoxy groups are attached to the rest of the molecule via the oxygen atom in that group.

In the respect, compounds of the invention may exhibit tautomerism. All tautomeric forms and mixtures thereof are included within the scope of the invention.

In the above formula, the carrier Y is selected from cellulose, starch, dextran, agar, agarose, polyacrylamide, poly (meth)acrylate, a polyvinyl hydrophilic polymer, polystyrene and polysulfone, silica, alumina, titania oxide, zirconia oxide, a polysaccharide-synthetic polymer, a polysaccharide-mineral structure, or a synthetic polymer-mineral structure.

In a preferred embodiment according to the invention, in the above formula, $R^1$ represents H, n represents 0, X represents NH and Y represents agarose.

Optionally, in the above formula a spacer molecule is located between X and Y, such as hexamethylenediamine or aminocapronic acid.

In a further preferred embodiment, $R^1$ represents H, n represents 0, X represents NH, Y represents HP-Sepharose, and the spacer molecule, if present, is hexamethylene diamine. The carrier material Y is a chromatographic carrier material of any shape and may be in the form of beads, irregularly shaped particles, fibers, membranes, flat structure or porous mineral materials.

In a second aspect, the invention relates to a method of producing the above described chromatographic adsorbent, comprising the following steps:
a) providing a chromatographic carrier material Y; and
b) coupling a ligand on the surface of said carrier material, to produce an adsorbent of the formula

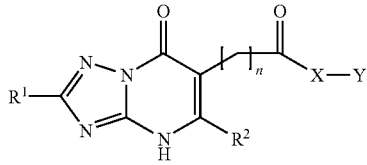

and its corresponding enol-form,
wherein
X represents O, S or NH;
$R^1$ represents H, $C_{1-6}$ alkyl, $C_{1-6}$ alkoxy, $C_{1-6}$ alkoxy-$C_{1-6}$ alkyl, Ar, —C(O)NHR$^3$, —C(O)—R$^3$ or halo;
$R^2$ represents H, $C_{1-3}$ alkyl or halo;
$R^3$ represents H, $C_{1-6}$ alkyl, $C_{1-6}$ alkoxy, $C_{1-6}$ alkoxy-$C_{1-6}$ alkyl or Ar;
n represents 0, 1, 2 or 3;
Y represents a carrier.
Ar represents a $C_{6-10}$ aryl group, which group is optionally substituted by one or more substituents selected from —OH, cyano, halo, nitro, $C_{1-6}$ alkyl and alkoxy;
The carrier Y is substituted with X=NH$_2$ or SH, or OH.
Preferably, the carrier Y is an amine possessing matrix. The carrier may also be a thiol possessing matrix or hydroxyl possessing matrix.

More preferably, the carrier Y is epichloro hydrine activated HP-Sepharose extended with hexamethylene diamine.

In a third aspect, the invention relates to use of an adsorbent described above for separating substances by affinity chromatography. The preferred use is for separating IgG, fragments thereof and/or complexes involving IgG or fragments thereof. The IgG may be monoclonal IgG, polyclonal IgG, or recombinant IgG or fragments thereof. The complexes may be immune complexes or fusion proteins involving IgG. The adsorbent may be used for all subclasses of IgG and fragments thereof. The separated IgG may be used for therapeutic, diagnostic, research and development purposes or be used as affinity handles in e.g. chromatography.

In silico techniques were used for identifying a suitable conserved and generic binding cleft on the Fc-part of IgG. Thereafter a virtual screening of commercially available substances was performed in order to identify potential binders to this cleft. The potential binding structures were ordered and tested for binding and selectivity with an in vitro procedure based on STD-NMR and surface plasmon resonance (SPR) analysis.

This procedure identified one structure showing interesting chromatographic properties.

The identified binding structure was attached to a chromatographic resin and evaluated for binding towards IgG. It was found that the ligand showed a generic binding for IgG.

Generic binding of IgG means binding of all IgG subclasses, i.e. IgG1, IgG2, IgG3, IgG4.

DETAILED DESCRIPTION OF THE INVENTION

Figure 1:
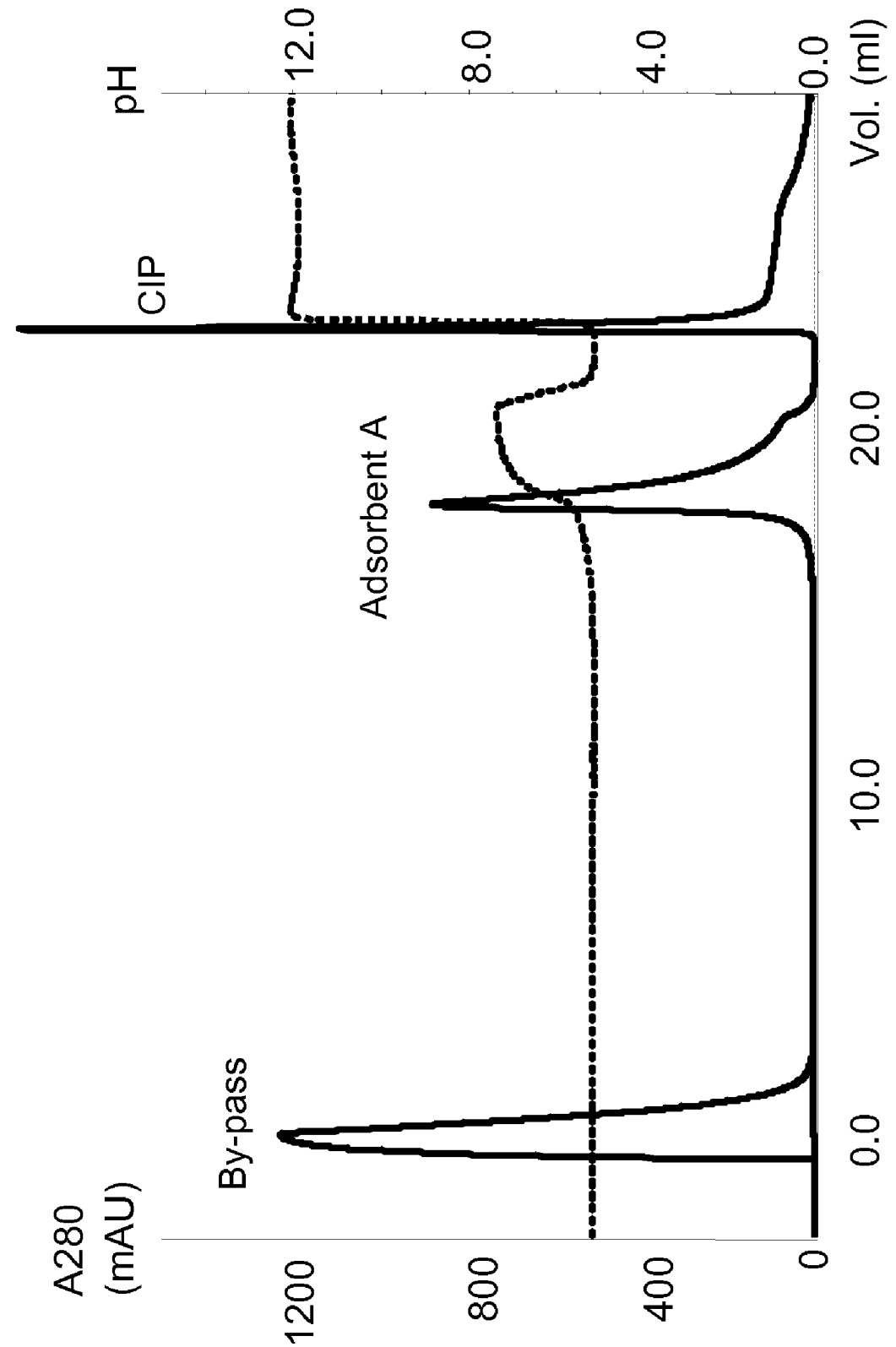
FIG. 1 shows an elution protein profile of injected polyclonal IgG on an adsorbent according to the invention. The dotted line represents pH in the eluent.

The invention will now be described more closely in association with in silico and wet experiments.

Identification of Suitable IgG Binding Site

A cleft on the Fc fragment of human IgG was identified as a putative target docking site for small organic molecules by screening of the protein surface with molecular modelling technologies using the Protein Data Bank (pdb) structure with code 1dn2 (Delano et al. 2000).

Two symmetry-related channels were identified which arise from deeper clefts at the interface between the symmetry related molecules. These clefts are rather hydrophilic containing polar groups on their surface. Each one of the two symmetry related clefts can be used as (equivalent) sites for virtual screening. The identified site was substantially conserved among the members of the IgG family from human sources.

Docking Simulations

Compounds from databases for virtual screening were docked to the identified cleft and resulted in a total of 119 diverse compounds which were identified as putative binders. The protein structure used for the docking simulations was the 1.65 Å structure of Fc in complex with Z34C (pdb code 1I6x; Idusogie et al. 2000) because of its superior resolution. The dimer was generated from the crystallographic symmetry with the program O (Jones et al. 1991). The best ranked conformation and its FlexX (Rarey et al 1996) score were saved for each molecule.

Selection of Docked Molecules (Ligand Molecules)

All compounds producing a docking conformation with an estimated free energy of binding more negative than −20 kJ/mol were visually inspected with respect to complementarity to the surface of the cleft in hydrophobicity, hydrogen bonding pattern, charges and conformation. In addition, rigidity was considered an advantage whereas short contacts and strained geometry were considered disadvantageous.

NMR and SPR Screening of Potential Ligands

From the virtual screening 166 compounds were suggested as potential binders to the identified cleft. After further manual selection (based on assumed stability, reactivity and availability) compounds were order for testing. Eventually 69 compounds arrived and were assigned an individual internal identification number before entering the screening procedure.

The screening procedure was based on in vitro screening using two independent in solution analytical techniques relying on saturation difference transfer NMR (STD NMR) and Surface Plasmon Resonace (SPR) methods.

In the NMR screen 69 substances were tested for affinity towards two different monoclonal antibodies (MAbs) and a commercially available Fc-fragment. Unspecific protein binding was investigated by testing for affinity towards α-amylase. Compounds that were found having affinity towards all three IgG related proteins, but no affinity towards α-amylase were assigned as potential candidates for affinity ligands towards the Fc-part of IgG.

In the SPR screen 53 compounds were tested (non-soluble substances were excluded) for affinity towards a monoclonal antibody and a commercially available Fc-fragment. Analysis data were corrected for the different molecular weights and are presented as percentage of the theoretical maximal response.

In order to select potential candidates for further investigations SPR data were arranged in such a way that all substances with a response higher than 10% for both Fc fragment and IgG were selected as potential candidates. These compounds were compared with the ones indicated by the NMR-screening. It turned out that most of the SPR derived hits had been rejected in NMR screen due to unspecific binding towards α-amylase. One compound was selected as potential affinity candidate by both methods; compound I, see below.

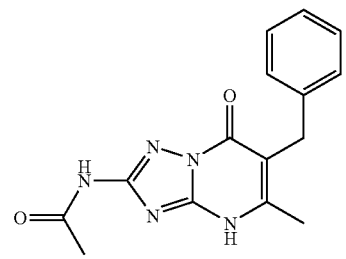

Further structures (commercially available compounds) surrounding compound I were investigated in solution in order to optimize the affinity ligand candidate. These compounds were subject to a corresponding SPR and NMR analysis for affinity as was presented above. However this time only the Fc-fragment was used in the NMR screening while the SPR analysis was performed with the corresponding test proteins as in the first selection.

The selected structures should be positive by NMR and also have a high ranking for affinity towards IgG molecule as indicated by SPR and at least medium ranking for affinity towards Fc-fragment. Compounds showing unspecific binding towards HSA were excluded. This selection emerged in a final candidate, Compound II. This compound also had the potential for a straight forward coupling chemistry allowed via the (ester protected) carboxylic acid functionality.

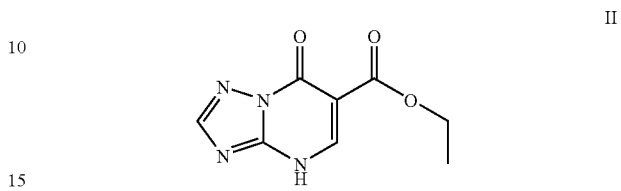

The hit compound from the library, ligand II is in ketoform. The ligand screened in solution and coupled to gel exists as the equilibrium between the ketoform and the enolform.

The relation between the keto and enol form is affected by several parameters such as solvent, concentration, and temperature. All tautomeric forms and mixtures thereof are included within the scope of the invention.

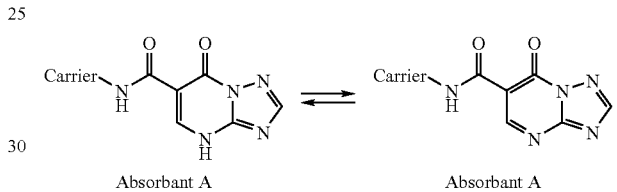

Production of Chromatographic Adsorbent

The production of an adsorbent of the invention will now be described in an exemplifying but not limiting way. The choice of coupling reagents and carriers may be varied within broad limits and is well known to the person skilled in the art.

Coupling of Selected Ligand (Compound II) to Chromatographic Matrix (Carrier)

The identified candidate compound II is commercially available and was used for coupling. Compound II was attached to an amine possessing matrix or carrier via its carboxylic acid functionality using any conventional amid formatting reagent, such as O-(7-Azabenzotriazol-1-yl)-N,N,N',N'-tetramethyluronium hexafluorophosphate (HATU), N,N'-Dicyclohexylcarbodiimide (DCC), N-(3-Dimethylaminopropyl)-N'-ethylcarbodiimide (EDC), 1-Hydroxybenzotriazole (HOBt), acid chloride formatting reagent or combinations thereof in the presence of a suitable base, such as diisopropylethyl amine, triethyl amine or potassium carbonate. The carrier used was an epichloro hydrine activated HP-Sepharose bead extended with hexamethylene diamine. The coupling transformed the ester functionality from the Compound II into an amide functionality, which should result in a minimum of change of steric and electronic alteration from the in solution tested ester functionality.

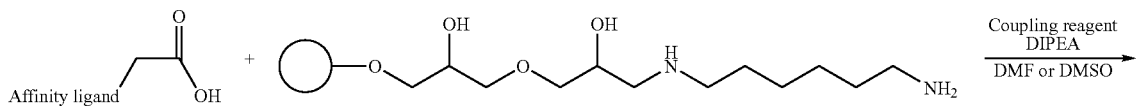

Structure of Adsorbent A (carrier + spacer ligand II)

Adsorbent A comprises either the keto or the enol form, or a mixture of the keto and enol form, as described in the equilibrium formula above of Adsorbent A.

The outcome of the coupling was determined using a standard MAS NMR method to 7 μmol/mL.

Chromatography Using Adsorbent A 0.5 mL Adsorbent A was packed into a Tricorn 5/20 column and was equilibrated with 0.1 M acetate, 0.137 M NaCl, pH 5.0.

Polyclonal IgG (Gammanorm) (1 mg in 1 ml buffer) was injected to the Adsorbent A-column using 0.1 M acetate, 0.137 M NaCl, pH 5.0 as binding buffer.

The peak in FIG. 1 at 1 ml represents the protein injected by-pass the column. Generic binding of polyclonal IgG was observed. 56-65% of the polyclonal IgG was eluted with PBS, pH 7.4 at 18 mL. The recovery was determined by calculation of protein concentration in collected fractions, and by integration and calculation of the ratio between the eluted peak area and the by-pass peak area. The rest of the bound protein was released during CIP in a sharp peak at 23 ml. Dotted line shows pH in eluent.

In an alternative buffer system (0.1 M HAc, 50 mM phosphate pH 5.0) the dynamic binding capacity was determined to 24 mg/mL.

The results in FIG. 1 show that the adsorbent of the present invention may be used for generic binding of IgG.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for affinity chromatography, comprising the step of selectively adsorbing IgG, fragments thereof and/or complexes involving IgG or fragments thereof on a chromatographic adsorbent, using a compound comprising the following formula and its corresponding enol-form,
wherein
X represents O, S, or NH;
$R^1$ represents H, $C_{1-6}$ alkyl, $C_{1-6}$ alkoxy, $C_{1-6}$ alkoxy-$C_{1-6}$ alkyl, Ar, —C(O)NHR$^3$, —C(O)—R$^3$ or halo;
$R^2$ represents H, $C_{1-3}$ alkyl or halo;
$R^3$ represents H, $C_{1-6}$ alkyl, $C_{1-6}$ alkoxy, $C_{1-6}$ alkoxy-$C_{1-6}$ alkyl or Ar;
n represents 0, 1, 2 or 3;
Y represents a carrier;
Ar represents a $C_{6-10}$ aryl group, which group is optionally substituted by one or more substituents selected from —OH, cyano, halo, nitro, $C_{1-6}$ alkyl and alkoxy.

2. The method of claim 1, wherein the carrier Y is selected from cellulose, starch, dextran, agar, agarose, polyacrylamide, poly(meth)acrylate, a polyvinyl hydrophilic polymer, polystyrene and polysulfone, silica, alumina, titania oxide, zirconia oxide, a polysaccharide-synthetic polymer, a polysaccharide-mineral structure, or a synthetic polymer-mineral structure.

3. The method of claim 1, wherein $R^1$ represents H, n represents 0, X represents NH and Y represents agarose.

4. The method of claim 3, further comprising a spacer molecule between X and Y.

5. The method of claim 4, wherein Y represents HP-Sepharose, and hexamethylene diamine is the spacer molecule.

6. The method of claim 1, further comprising a spacer molecule between X and Y.

7. The method of claim 6, wherein $R^1$ represents H, n represents 0, X represents NH, Y represents HP-Sepharose, and hexamethylene diamine is the spacer molecule.

8. The method of claim 1, wherein the carrier material Y is in the form of beads, irregularly shaped particles, fibers, membranes, flat structure or porous mineral materials.

* * * * *